US011229899B2

(12) United States Patent
Li et al.

(10) Patent No.: US 11,229,899 B2
(45) Date of Patent: Jan. 25, 2022

(54) CATALYST COMPOSITION

(71) Applicant: SHELL OIL COMPANY, Houston, TX (US)

(72) Inventors: Hong-Xin Li, Lansdale, PA (US); Richard Berend Mauer, Amsterdam (NL); Gisela Sabater Pujadas, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 16/467,635

(22) PCT Filed: Dec. 7, 2017

(86) PCT No.: PCT/EP2017/081875
§ 371 (c)(1),
(2) Date: Jun. 7, 2019

(87) PCT Pub. No.: WO2018/104471
PCT Pub. Date: Jun. 14, 2018

(65) Prior Publication Data
US 2020/0078777 A1    Mar. 12, 2020

Related U.S. Application Data

(60) Provisional application No. 62/431,860, filed on Dec. 9, 2016.

(51) Int. Cl.
*B01J 29/80*    (2006.01)
*B01J 23/42*    (2006.01)
*B01J 29/22*    (2006.01)
*B01J 29/44*    (2006.01)
*B01J 35/00*    (2006.01)
*B01J 35/02*    (2006.01)
(Continued)

(52) U.S. Cl.
CPC ............... *B01J 29/80* (2013.01); *B01J 23/22* (2013.01); *B01J 23/26* (2013.01); *B01J 23/28* (2013.01); *B01J 23/30* (2013.01); *B01J 23/34* (2013.01); *B01J 23/36* (2013.01); *B01J 23/42* (2013.01); *B01J 23/44* (2013.01); *B01J 23/464* (2013.01); *B01J 29/18* (2013.01); *B01J 29/185* (2013.01); *B01J 29/22* (2013.01); *B01J 29/24* (2013.01); *B01J 29/26* (2013.01); *B01J 29/40* (2013.01); *B01J 29/405* (2013.01); *B01J 29/44* (2013.01); *B01J 29/46* (2013.01); *B01J 29/48* (2013.01); *B01J 35/002* (2013.01); *B01J 35/0066* (2013.01); *B01J 35/023* (2013.01); *B01J 37/0009* (2013.01); *B01J 37/0018* (2013.01); *B01J 37/0201* (2013.01); *B01J 37/04* (2013.01); *B01J 37/088* (2013.01); *C01B 39/023* (2013.01); *C07C 6/126* (2013.01); *B01J 2229/18* (2013.01); *B01J 2229/186* (2013.01); *B01J 2229/20* (2013.01); *B01J 2229/42* (2013.01); *C01P 2004/64* (2013.01); *C07C 2523/42* (2013.01); *C07C 2529/18* (2013.01); *C07C 2529/22* (2013.01); *C07C 2529/24* (2013.01); *C07C 2529/26* (2013.01); *C07C 2529/40* (2013.01); *C07C 2529/44* (2013.01); *C07C 2529/46* (2013.01); *C07C 2529/48* (2013.01); *C07C 2529/80* (2013.01); *Y02P 20/52* (2015.11)

(58) Field of Classification Search
CPC .... B01J 35/002; B01J 35/0066; B01J 35/023; B01J 37/088; B01J 37/04; B01J 37/0201; B01J 37/0009; B01J 29/18; B01J 29/185; B01J 29/22; B01J 29/24; B01J 29/26; B01J 29/80; B01J 29/40; B01J 29/405; B01J 29/44; B01J 29/46; B01J 29/48; B01J 2229/18; B01J 2229/186; B01J 2229/20; B01J 2229/42; B01J 23/42; B01J 23/464; B01J 23/44; B01J 23/22; B01J 23/26; B01J 23/28; B01J 23/30; B01J 23/34; B01J 23/36; C01B 39/38; C01B 39/023; C01B 39/026; C01B 39/26; C07C 2529/40; C07C 2529/44; C07C 2529/46; C07C 2529/48; C07C 2529/18; C07C 2529/80; C07C 2529/22; C07C 2529/24; C07C 2529/26; Y02P 20/52; C01P 2004/64
USPC ......... 502/63, 64, 66, 67, 69, 71, 74, 77, 78
See application file for complete search history.

(56) References Cited

U.S. PATENT DOCUMENTS

| 3,702,886 A | 11/1972 | Argauer et al. |
| 4,511,547 A | 4/1985 | Iwayama et al. |

(Continued)

FOREIGN PATENT DOCUMENTS

| WO | 2009158233 A2 | 12/2009 |
| WO | 2009158244 A2 | 12/2009 |

OTHER PUBLICATIONS

International Search Report and Written Opinion received for PCT Patent Application No. PCT/EP2017/081875 dated Mar. 22, 2018, 10 pages.

(Continued)

*Primary Examiner* — Elizabeth D Wood
(74) *Attorney, Agent, or Firm* — Shell Oil Company

(57) ABSTRACT

A catalyst composition comprising (a) carrier comprising (i) 5 to 95 wt % mordenite type zeolite having a mean crystallite length parallel to the direction of the 12-ring channels of 60 nm or less and a mesopore volume of at least 0.10 cc/gram, (ii) 5 to 95 wt % ZSM-5 type zeolite; and (iii) 10 to 60 wt % inorganic binder; and (b) 0.001 to 10 wt % of one or more catalytically active metals, wherein the inorganic binder comprises titania, its preparation and its use in alkylaromatic conversion.

11 Claims, No Drawings

(51) Int. Cl.
  *B01J 37/00* (2006.01)
  *B01J 37/02* (2006.01)
  *B01J 37/04* (2006.01)
  *B01J 37/08* (2006.01)
  *C01B 39/02* (2006.01)
  *C07C 6/12* (2006.01)
  *B01J 29/40* (2006.01)
  *B01J 29/18* (2006.01)
  *B01J 29/26* (2006.01)
  *B01J 29/24* (2006.01)
  *B01J 29/48* (2006.01)
  *B01J 29/46* (2006.01)
  *B01J 23/26* (2006.01)
  *B01J 23/46* (2006.01)
  *B01J 23/22* (2006.01)
  *B01J 23/28* (2006.01)
  *B01J 23/44* (2006.01)
  *B01J 23/30* (2006.01)
  *B01J 23/36* (2006.01)
  *B01J 23/34* (2006.01)

(56) References Cited

U.S. PATENT DOCUMENTS

| | | | |
|---|---|---|---|
| 6,867,340 B2 | 3/2005 | Oh et al. | |
| 7,626,064 B1 * | 12/2009 | Boldingh | B01J 29/26 585/475 |
| 8,889,940 B2 | 11/2014 | Bogdan et al. | |
| 9,365,469 B2 | 6/2016 | Lafyatis et al. | |
| 2012/0083635 A1 | 4/2012 | Boldingh et al. | |
| 2013/0090507 A1 | 4/2013 | Ali | |
| 2016/0221896 A1 * | 8/2016 | Elia | B01J 29/7484 |

OTHER PUBLICATIONS

Baerlocher et al., "Atlas of Zeolite Framework Types", Sixth Revised Edition, 2007, 6 Pages.

Moulijn et al., "Catalysis : An Integrated Approach to Homogeneous, Heterogeneous and Industrial Catalysis", Studies in Surface Science and Catalysis, vol. 79, Chapter 10, 1993, pp. 363-400.

* cited by examiner

CATALYST COMPOSITION

CROSS REFERENCE TO RELATED APPLICATIONS

This is a national stage application of International Application No. PCT/EP2017/081875 filed 7 Dec. 2017, which claims benefit of priority to U.S. Provisional Application No. 62/431,860, filed 9 Dec. 2016.

FIELD OF THE INVENTION

The present invention is directed to a catalyst composition, its preparation and its use in alkylaromatic conversion, more specifically transalkylation.

BACKGROUND TO THE INVENTION

Ethylbenzene is one of the aromatic hydrocarbons that can be obtained from naphtha pyrolysis or reformate. Reformate is an aromatic product obtained by the catalyzed conversion of straight-run hydrocarbons boiling in the 70 to 190° C. range, such as straight-run naphtha. The catalysts used for the production of reformate are often platinum-on-alumina catalysts. The reformate feedstock itself is obtained by fractionation or distillation of crude petroleum oil, its composition varying depending on the source of the crude oil, but generally having a low aromatics content. On conversion to reformate, the aromatics content is considerably increased and the resulting hydrocarbon mixture becomes highly desirable as a source of valuable chemical intermediates and as a component for gasoline. The principle components are a group of aromatics often referred to as BTX: benzene, toluene and the xylenes, including ethylbenzene. Other components may be present such as their hydrogenated homologues, e.g. cyclohexane.

Of the BTX group the most valuable components are benzene and the xylenes, and therefore BTX is often subjected to processing to increase the proportion of those two aromatics: hydrodealkylation of toluene to benzene and toluene disproportionation to benzene and xylenes. Within the xylenes, para-xylene is the most useful commodity and xylene isomerisation or transalkylation processes have been developed to increase the proportion of para-xylene.

A further process that can be applied is the hydrodealkylation of ethylbenzene to benzene.

Generally, it is preferred to isolate BTX from the reformate stream, and subject the BTX stream to xylene isomerisation with the aim of maximising the para-xylene component. Xylene isomerisation is a catalytic process. Some catalysts used in this process have the ability to not just isomerise xylenes but to simultaneously dealkylate the ethylbenzene component. Normally the para-xylene is then separated out to leave benzene, toluene (unless one or more toluene conversion processes have already been applied) and the remaining mixed xylenes, including ethylbenzene. This BTX stream can be converted by (i) dealkylation to selectively eliminate ethylbenzene and to increase the yield of benzene while isomerizing xylenes to equilibrium or (ii) further reforming to convert ethylbenzene to xylenes while isomerizing xylenes to equilibrium or (iii) transalkylation by isomerizing xylenes to equilibrium and dealkylating specific alkylaromatic compounds. The latter process is the subject of the present invention.

WO 2009/158233 A2 describes a so-called UZM-14 aggregate material comprising globular aggregates of crystallites having a MOR framework type with a mean crystallite length parallel to the direction of 12-ring channels of 60 nm or less and a mesopore volume of at least 0.10 cc/g. In one preferred embodiment, said aggregate material is disclosed in combination with a binder selected from one or more of alumina, silica and silica-alumina.

Example 1 in WO 2009/158233A2 describes catalysts comprising a so-called UZM-14 aggregate material in combination with alumina binder and rhenium as dopant and testing of said catalysts in the transalkylation of a feedstock comprising toluene and various C9/C9+ aromatic compounds is outlined in Example 2.

Example 4 in WO 2009/158233 A2 describes catalysts comprising a so-called UZM-14 aggregate material in combination with a MFI zeolite and alumina binder and nickel and molybdenum as metal dopants and the testing of said catalysts in the transalkylation of a feedstock comprising toluene and various C9/C9+ aromatic compounds.

WO 2009/158244 A2 also describes a transalkylation process using a catalyst comprising so-called UZM-14 aggregate material comprising globular aggregates of crystallites having a MOR framework type with a mean crystallite length parallel to the direction of 12-ring channels of 60 nm or less and a mesopore volume of at least 0.10 cc/g in combination with a binder selected from one or more of alumina, silica and silica-alumina. The Examples in WO 2009/158244 A2 are broadly similar to those in WO 2009/158233 A2.

SUMMARY OF THE INVENTION

It is an aim to provide an improved catalyst which can be used in an alkylaromaticc onversion process, more spefi- cially transalkylation, a process for preparing such catalyst and a process in which such catalyst is used.

The present invention relates to a catalyst composition comprising (a) a carrier comprising (i) mordenite type zeolite having a mean crystallite length parallel to the direction of the 12-ring channels of 60 nm or less and a mesopore volume of at least 0.10 cc/gram in an amount in the range of from 5 to 95 wt %, based on total weight of carrier, (ii) ZSM-5 type zeolite in an amount of from 5 to 95 wt %, based on total weight of carrier; and (iii) an inorganic binder in an amount in the range of from 10 to 60 wt %, based on total weight of carrier; and (b) of from 0.001 to 10 wt % of one or more catalytically active metals, wherein the inorganic binder comprises titania.

The present invention further relates to a process for preparing such catalyst composition, comprising the steps of: (a) mixing the mordenite type zeolite, ZSM-5 type zeolite and inorganic binder and extruding the mixture obtained, (b) optionally subjecting the extrudates obtained in step (a) to a heat treatment, (c) impregnating the calcined extrudates with a solution comprising one or more catalytically active metals, and (d) optionally subjecting the impregnated extrudates obtained in step (c) to a heat treatment.

The present invention further relates to a process for the conversion of a feedstock containing alkylaromatic hydrocarbons using a catalyst according to the invention or prepared by a process according to the invention.

DETAILED DESCRIPTION OF THE INVENTION

In alkylaromatic conversion, more specifically transalkylation by isomerizing xylenes to equilibrium and dealkylating specific alkylaromatic compounds, it can be advantageous if a catalyst has a high activity in producing xylene.

Furthermore, it can be advantageous in such transalkylation if the product contains benzene of high purity. The purity of benzene is the amount of benzene in the fraction boiling in the benzene boiling range in the product. The process of the present invention allows to produce benzene of high purity. Furthermore, limited aromatics loss has been observed when the catalyst was used in alkylaromatic conversion.

Mordenite type type zeolite and ZSM-5 type zeolite are well known in the art. For the present application, these zeolites are as defined and described in "Atlas of Zeolite Framework Types," ed. Baerlocher et al., Sixth Revised Edition (Elsevier 2007).

A preferred mordenite type zeolite for use in the present invention has been described in WO 2009/158244 A2.

The average particle size of the zeolites described herein is determined by calculating the number average particle size of a sample which has been measured by using X-ray diffraction (line broadening) and the Scherrer equation. This technique is well known in the art for determining crystallite particle size (see, for example, "Catalysis: An Integrated Approach to Homogeneous, Heterogeneous and Industrial Catalysis", J. A. Moulijn, P. W. N. M. van Leeuwen, R. A. van Santen (Eds.), Elsevier, 1993, pp. 365-367, WO 2009/158244 A2).

Specifically, the mordenite zeolite of the present invention preferably has a mean crystallite length of from 10 to 60, more preferably 20 to 40. The mean crystallite length parallel to the direction of the 12-ring channels is to be measured by applying the Scherrer equation to x-ray diffraction data. Prior to analysis, the mordenite is to be converted to the hydrogen form by heating the $NH_4$-exchanged form to 540° C. for 2 hours in nitrogen and then for 5 hours in air. Specifically, the full width at half maximum (FWHM) is to be measured for the (002) diffraction peak at 23.8° 2θ for CuKα radiation and then the mean crystallite length, L0002, parallel to the direction of the 12-ring channels was calculated from the Scherrer equation. It is assumed that the peaks are partially Gaussian and partly Cauchy in shape.

Additionally, the mordenite type zeolite has a mesopore volume of at least 0.10 cc/g. Preferably, the mordenite type zeolite has a mesopore volume of at most 0.23 cc/g. The mesopore volume is determined from nitrogen sorption isotherms as follows. Prior to analysis, the mordenite is converted to the hydrogen form by heating the $NH_4$-exchanged form to 550° C. for 5 hours in air. The sorption isotherms are then measured and the total pore volume is determined from the nitrogen uptake at the highest value of P/PO (about 0.98). The micropore volume is estimated using the t-plot. Taking the data from the desorption isotherm, the mesopore volume is calculated from the sum of gas adsorbed on the zeolite over the following range of pore sizes: 600-260 radial angstroms (macropores), 260-100 radial angstroms (mesopores), 100-50 radial angstroms (micropores), and 50-20 radial angstroms.

The catalyst composition according to the present invention comprises a carrier which preferably comprises mordenite type zeolite in an amount of from 20 to 90 wt %, based on total weight of carrier. Preferably, the mordenite type zeolite is present in an amount in the range of from 30 to 70 wt %, more preferably in the range of from 40 to 60 wt %, based on total weight of carrier.

The present catalyst composition comprises a carrier which preferably comprises a ZSM-5 type zeolite in an amount of 10 to 70 wt %, based on total weight of carrier material compound. Preferably, the ZSM-5 type zeolite is present in an amount in the range of from 15 to 60 wt %, more preferably in the range of from 20 to 40 wt %, based on total weight of carrier.

The ZSM-5 type zeolite preferably has a silica to alumina molar ratio in the range of from 10 to 50, preferably in the range of 15 to 40, and more preferably in the range of from 18 to 35.

The ZSM-5 type zeolite preferably has a number average particle size in the range of 20 to 500 nm. Preferably, the ZSM-5 type zeolite has a number average particle size in the range of from 25 to 300 nm, more preferably in the range of from 25 to 200 nm and even more preferably in the range of from 30 to 200 nm. The average particle size is determined as hereinbefore described by using X-ray diffraction (line broadening) and the Scherrer equation.

In a particularly preferred embodiment of the present invention, the ZSM-5 type zeolite has a number average particle size in the range of from 25 to 100 nm, more preferably in the range of from 30 to 100 nm, and even more preferably in the range of from 30 to 70 nm. It has been surprisingly observed that use of a small average particle for the ZSM-5 type zeolite in combination with the other features of the present catalyst composition can further improve the benzene purity.

Suitable ZSM-5 type zeolites to be used in accordance with the present invention can be prepared as, for example, described in U.S. Pat. Nos. 3,702,886 A and 4,511,547 A. Suitable examples of ZSM-5 type zeolites include CBV 3014E, CBV 3020E and CBV 8014, available commercially from Zeolyst International.

In a preferred embodiment of the present invention, the catalyst composition, as hereinbefore described, comprises
(a) a carrier comprising (i) mordenite type zeolite having a mean crystallite length parallel to the direction of the 12-ring channels of 60 nm or less and a mesopore volume of at least 0.10 cc/gram in an amount in the range of from 5 to 95 wt %, based on total weight of carrier, (ii) ZSM-5 type zeolite in an amount of from 5 to 95 wt %, based on total weight of carrier; and (iii) an inorganic binder in an amount in the range of from 10 to 60 wt %, based on total weight of carrier; and
(b) of from 0.001 to 10 wt % of one or more catalytically active metals,
wherein the inorganic binder consists of titania.

The catalyst composition according to the present invention preferably contains the titania as inorganic binder in an amount in the range of from 10 to 50 wt %, based on total weight of carrier. Preferably, the inorganic binder is present in an amount in the range of from 10 to 40 wt %, more preferably in the range of from 15 to 30 wt %, based on total carrier.

In shaped form, for example as extrudates, the carrier generally has a BET surface area falling in the range of from 200 to 600 m2/g, preferably 250 to 500 m2/g, more preferably from 350 to 450 m2/g. The surface area suitably is measured according to ASTM D3663-03(2015). Furthermore, the extrudates preferably have a pore volume, by mercury intrusion, in the range of from 0.2 to 1.2 ml/g, preferably 0.3 to 1.0 ml/g, more preferably 0.4 to 0.8 ml/g.

The present catalyst composition may be shaped in any particular form. Suitable shapes include trilobes and cylinders.

Preferably, the present catalyst composition is in the shape of trilobes.

The carrier can be prepared by shaping the carrier and subsequently subjecting the carrier to a heat treatment. The heat treatment preferably comprises calcining the shaped carrier optionally preceded by drying. Drying temperatures can suitably be in the range of from 50 to 200° C. Drying times can suitably be in the range of from 0.5 to 24 hours. Calcination temperatures can suitably be in the range of from 200 to 800° C., preferably in the range of from 300 to 600° C. In the calcination of the carrier material, a relatively short time can suitably be applied such as in the range of from 0.5 to 5 hours. The calcination can suitably be carried out at a temperature in the range of from 400 to 750° C., preferably in the range of from 450 to 700° C., more preferably in the range of from 500 to 700° C.

The present catalyst composition comprises one or more catalytically active metals. These metals preferably are chosen from the group consisting of Groups 2-14 of the IUPAC Periodic Table of Elements dated 1 May 2013. Preferably, the catalyst composition comprises one or more metals chosen from the group consisting of tin, tungsten, vanadium, molybdenum, rhenium, nickel, cobalt, chromium, manganese, platinum and palladium.

The carrier can be prepared by mixing the mordenite, the ZSM-5 type zeolite and the inorganic binder, shaping the mixture and subjecting the shaped mixture to calcination at a temperature of from 200 to 800° C. The shaped mixture can be dried before calcination. Drying temperatures can suitably be in the range of from 50 to 200° C. Drying times can suitably be in the range of from 0.5 to 24 hours. Calcination temperatures can suitably be in the range of from 200 to 800° C., preferably in the range of from 300 to 600° C. In the calcination of the carrier material, a relatively short time can suitably be applied such as in the range of from 0.5 to 5 hours. The calcination can suitably be carried out at a temperature in the range of from 400 to 700° C., preferably in the range of from 450 to 600° C.

The amount of metal preferably is in the range of from 0.001 to 10 wt %, as metal based on total weight of catalyst, more preferably in the range of from 0.1 to 10 wt %, more preferably in the range of from 2 to 9 wt %, more preferably of from 2 to 8 wt %, more preferably of from 2 to 6 wt % of metal based on total weight of catalyst. The metals can be incorporated in the carrier with the help of a metal salt solution. Preferably, the metals are incorporated by pore volume impregnation.

The amount of metal is calculated as metal independent from the actual compound present.

The catalyst composition according to the invention can suitably have such shape that a reactor filled with the catalyst particles has an average void fraction of at least 10% by volume, preferably in the range of from 20 to 70%, more preferably in the range of from 35 to 55% by volume.

After incorporating the metal in the carrier, the impregnated carrier preferably is subjected to a heat treatment. This heat treatment preferably is of from 100 to at most 600° C., preferably of from 200 to at most 550° C.

Before use of the catalyst composition, it will be preferred that the metals on the catalyst composition are in metallic (and not oxidic) form. Accordingly, the catalyst composition preferably is subjected to reducing conditions, which are, for example, heating in a reducing atmosphere, such as in hydrogen optionally diluted by an inert gas, such as nitrogen or carbon dioxide, at temperature in the range of from 150 to 600° C. for a period of time in the range from 0.5 to 5 hours.

The present invention also relates to a process for the conversion, more specifically transalkylation, of a feedstock containing alkylaromatic hydrocarbons using a catalyst in accordance with the present invention.

Suitably, the alkylaromatic hydrocarbon feedstock comprises at least 30 wt % of total amount of toluene and alkylaromatics containing at least 9 carbon atoms, more specifically at least 40 wt %, more specifically at least 50 wt %, most specifically at least 90 wt %. Further compounds which can be present are ethylbenzene and xylene. Preferably, the feedstock comprises toluene and alkylaromatic compounds containing at least 9 carbon atoms in a weight ratio of from 10:90 to 90:10. Most preferably, the alkylaromatic hydrocarbon feedstock comprises of from 35 to 75 wt % of toluene and of from 25 to 65 wt % of alkylaromatic compounds containing at least 9 carbon atoms.

The feedstock suitably is contacted with the catalyst composition in the presence of hydrogen. This may be carried out in a fixed bed system, a moving bed system, or a fluidized bed system. Such systems may be operated continuously or in batch fashion. Preference is given to continuous operation in a fixed bed system. The catalyst may be used in one reactor or in several separate reactors in series or operated in a swing system to ensure continuous operation during catalyst change-out.

The present transalkylation process preferably is carried out at a temperature in the range of from 200 to 600° C., preferably in the range of from 250 to 500° C., and more preferably in the range of from 300 to 400 C. °.

The process preferably is carried out at a pressure in the range of from 1 to 50 barg, preferably at a pressure in the range of from 10 to 40 barg, and more preferably at a pressure in the range of from 25 to 35 barg.

The weight space velocity applied in the process is suitably in the range of from 0.2 to 30 hr, preferably from 2 to 20 hr-1, and more preferably in the range of from 3 to 6 hr-1.

The feed to hydrogen ratio mol.mol-1 is in the range of from 0.5 to 100, preferably in the range of from 1 to 10.

The reaction effluent preferably will be recovered and subjected to a distillation treatment to remove the desired products, more specifically xylene and benzene. Unreacted reactant such as for instance toluene can suitably be recycled for further reaction.

The present disclosure is not limited to the embodiments as described above and the appended claims. Many modifications are conceivable and features of respective embodiments may be combined.

The following examples of certain aspects of some embodiments are given to facilitate a better understanding of the present invention. In no way should these examples be read to limit, or define, the scope of the invention.

EXAMPLES

Example 1. Catalyst Preparation

A series of catalysts were prepared comprising a mixture of two zeolites, mordenite and ZSM-5, in their ammonium form (available from Zeolyst International), inorganic binder and platinum and Group 14 metal dopant as catalytically active metals. Each of the catalysts prepared contained analogous quantities of platinum and the Group 14 metal dopant as catalytically active metals. Said catalytically active metals were incorporated per U.S. Pat. No. 6,867,340 B2.

The catalysts were prepared by following the same general procedure, wherein, for example, by mixing 18 g of mordenite (either Mordenite-A or Mordenite-B, see Table 2 below) (in ammonium form), 12 g of ZSM-5 (either ZSM-5 A or ZSM-5 B, see Table 2 below) (in ammonium form) with binder (either alumina (available ex. Sasol), zirconia (available ex. Diachi) or titania (available ex. Evonik Industries)).

The powders were peptized together with metal salt solution comprising platinum and the Group 14 metal dopant. The peptized mixture was extruded to obtain particles having a diameter of 1.6 mm. These extrudates were dried at 120° C. for 2 hours followed by calcination in air of the sample at 500° C. for 2 hours.

A full overview of the catalysts prepared is given in Table 2, hereinbelow.

Example 2. Catalyst Testing

Catalysts prepared in Example 1 were tested in the production of benzene and mixed xylenes from a feed stock containing C9+ aromatic hydrocarbons by dealkylation and transalkylation.

A performance test was carried out for each of these samples in an aromatics transalkylation test and using feedstock summarized below in Table 1.

TABLE 1

| COMPONENT | CONTENT (wt %) |
| --- | --- |
| Toluene (C7) | 50.5 |
| Trimethylbenzenes (C9) | 28.6 |
| Ethyltoluenes (C9) | 11 |
| Propylbenzenes (C9) | 0.8 |
| Indane (C9) | 1.4 |
| Ethylxylenes (C10) | 7 |
| Tetramethylbenzenes (C10) | 0.5 |
| Remainder including compounds containing at least 10 carbon atoms + rest | 0.3 |

The performance test was performed once 10 g of the catalyst composition being tested had been charged in a fixed bed reactor and subjected first of all to a reduction step, at 400° C. for one hour in hydrogen atmosphere (>99% purity). Afterwards, the catalyst performance was measured in the fixed bed reactor under a total system pressure of 30 bars, a weight hourly space velocity of 3.5 g feed/g catalyst/hour and hydrogen to feed ratio of 4.5 mol.mol$^{-1}$. The temperature was varied to achieve the required conversion of 45% and the performance results are shown in Table 2 below.

TABLE 2

Catalyst Overview and Performances in Transalkylation

| | Catalyst 1 | Catalyst 2 | Catalyst 3 | Catalyst 4 | Comparative Catalyst 5 | Catalyst 6 |
| --- | --- | --- | --- | --- | --- | --- |
| CARRIER | | | | | | |
| Mordenite A (wt %)* | 50 | 50 | 50 | 50 | — | — |
| Mordenite B (wt %)** | — | — | — | — | 50 | 50 |
| ZSM-5 A (wt %)*** | 30 | — | — | — | — | — |
| ZSM-5 B (wt %)**** | — | 30 | 30 | 30 | 30 | 30 |
| Binder (wt %) | Alumina (20%) | Alumina (20%) | Titania (20%) | Zirconia (20%) | Alumina (20%) | Titania (20%) |
| CATALYST PERFORMANCE | | | | | | |
| Total conversion (%) | 45 | 45 | 45 | 45 | 45 | 45 |
| Relative Aromatic losses (mol %) | 100 | 51 | 48 | 96 | 48 | 21 |
| Relative % of co-boilers in benzene boiling point fraction | 100 | 63 | 46 | 162 | 27 | 23 |

*Mordenite A (SAR = 20; crystal size > 60 nm, mesopore volume ≥ 0.10 cc/gram).
**Mordenite B (SAR = 18; crystal size < 45 nm, mesopore volume ≥ 0.10 cc/gram).
***ZSM-5 A (SAR = 25; crystal size > 100 nm, specifically in range between 100-115 nm).
****ZSM-5 B (SAR = 30; crystal size < 100 nm, specifically in range between 25-40 nm).

The purity of the benzene may be considered as the amount of benzene in the fraction boiling at approximately the boiling point of benzene in the product. In this regard, the skilled person will understand that benzene does not have a boiling range per se but rather has a boiling point. However, benzene obtained by distillation will usually contain C6 and C7 non-aromatic hydrocarbon impurities that are difficult to separate from benzene by distillation because they have boiling points close to the boiling point of benzene. Hence, the fraction boiling at approximately the boiling point of benzene in the product will contain compounds containing 6 carbon atoms such as benzene, methyl-substituted cyclic compounds containing 5 carbons and cyclic compounds containing 6 carbon atoms. Thus, in Table 2, the % of co-boilers in the benzene boiling point fraction is a measure of the purity of the benzene and is given relative to the % of co-boilers in the benzene boiling point fraction when using reference Catalyst 1.

The aromatic loss is mol % aromatic compounds in the feed minus the mol % aromatic compounds in the product divided by the mol % aromatic compounds in the feed. This amount is given relative to the aromatic loss when using the reference catalyst (Catalyst 1).

The above experimental results in Table 2 show that catalyst according to the present invention surprisingly result in product having increased benzene purity and reduced loss of aromatic compounds.

Hence, the surprising benefit of using the specific mordenite as hereinbefore described in conjunction with ZSM-5 and titania as a binder is readily apparent in Table 2.

That which is claimed is:

1. A catalyst composition useful in the transalkylation and dealkylation of alkyaromatics, wherein the catalyst composition comprises:

(a) a carrier consisting essentially of: (i) mordenite type zeolite having a mean crystallite length parallel to the direction of the 12-ring channels of from 10 to 60 nm and a mesopore volume of at least 0.10 cc/gram in an amount in the range of from 20 to 90 wt %, based on total weight of carrier, (ii) ZSM-5 type zeolite having a silica-to-alumina molar ratio in the range of from 10 to 50 and present in an amount of from 10 to 70 wt %, based on total weight of carrier, wherein the ZSM-5 type zeolite has a number average particle size in the range of from 20 to 500 nm; and (iii) titania as a binder in an amount in the range of from 10 to 60 wt %, based on total weight of carrier; and (b) of from 0.001 to 10 wt % of one or more catalytically active metals selected from the group consisting of tin, tungsten, vanadium, molybdenum, rhenium, nickel, cobalt, chromium, manganese, platinum and palladium.

2. The catalyst composition according to claim 1, in which the carrier comprises mordenite type zeolite in an amount in the range of from 30 to 70 wt %, based on total weight of carrier.

3. The catalyst composition according to claim 1, in which the carrier comprises ZSM-5 type zeolite in an amount of from 15 to 60 wt %, based on total weight of carrier.

4. The catalyst composition according to claim 1, wherein the ZSM-5 type zeolite has a silica to alumina molar ratio in the range of from 15 to 40.

5. The catalyst composition according to claim 1, wherein the ZSM-5 type zeolite has a number average crystal size in the range of from 25 to 200 nm, as determined by X-ray diffraction.

6. The catalyst composition according to claim 1, wherein the catalytically active metals include platinum and tin.

7. A catalyst composition useful in the transalkylation and dealkylation of alkyaromatics, wherein the catalyst composition comprises:

(a) a carrier consisting essentially of: (i) mordenite type zeolite having a mean crystallite length parallel to the direction of the 12-ring channels of from 10 to 60 nm and a mesopore volume of at least 0.10 cc/gram in an amount in the range of from 20 to 90 wt %, based on total weight of carrier, (ii) ZSM-5 type zeolite having a silica-to-alumina molar ratio in the range of from 10 to 50 and present in an amount of from 10 to 70 wt %, based on total weight of carrier, wherein the ZSM-5 type zeolite has a number average crystal size in the range of from 25 to 200 nm, as determined by X-ray diffraction; and (iii) titania as a binder in an amount in the range of from 10 to 60 wt %, based on total weight of carrier; and (b) of from 0.001 to 10 wt % of one or more catalytically active metals selected from the group consisting of tin, tungsten, vanadium, molybdenum, rhenium, nickel, cobalt, chromium, manganese, platinum and palladium.

8. The catalyst composition according to claim 7, in which the carrier comprises mordenite type zeolite in an amount in the range of from 30 to 70 wt %, based on total weight of carrier.

9. The catalyst composition according to claim 7, in which the carrier comprises ZSM-5 type zeolite in an amount of from 15 to 60 wt %, based on total weight of carrier.

10. The catalyst composition according to claim 7, wherein the ZSM-5 type zeolite has a silica to alumina molar ratio in the range of from 15 to 40.

11. The catalyst composition according to claim 7, wherein the catalytically active metals include platinum and tin.

* * * * *